United States Patent
Shiffman et al.

(10) Patent No.: US 6,879,970 B2
(45) Date of Patent: Apr. 12, 2005

(54) APPARATUS AND METHOD FOR PREDICTION AND MANAGEMENT OF SUBJECT COMPLIANCE IN CLINICAL RESEARCH

(75) Inventors: Saul Shiffman, Pittsburgh, PA (US); Michael R. Hufford, Pittsburgh, PA (US); Jean A. Paty, Pittsburgh, PA (US)

(73) Assignee: invivodata, Inc., Scotts Valley, CA (US)

(*) Notice: Subject to any disclaimer, the term of this patent is extended or adjusted under 35 U.S.C. 154(b) by 897 days.

(21) Appl. No.: 09/825,534

(22) Filed: Apr. 2, 2001

(65) Prior Publication Data

US 2002/0143577 A1 Oct. 3, 2002

(51) Int. Cl.⁷ .............................................. G06F 15/18
(52) U.S. Cl. ......................................................... 706/21
(58) Field of Search ........................................... 706/21

(56) References Cited

U.S. PATENT DOCUMENTS

| | | | |
|---|---|---|---|
| D247,251 S | 2/1978 | Napoli | D24/17 |
| 4,262,632 A | 4/1981 | Hanton et al. | 119/1 |
| 4,353,375 A | 10/1982 | Colburn et al. | 128/782 |
| 4,367,752 A | 1/1983 | Jimenez et al. | 128/689 |
| 4,543,955 A | 10/1985 | Schroeppel | 128/635 |
| 4,566,461 A | 1/1986 | Lubell et al. | 128/668 |
| 4,592,018 A | 5/1986 | Wiegman | 365/63 |
| 4,686,624 A | 8/1987 | Blum et al. | 364/415 |

(Continued)

FOREIGN PATENT DOCUMENTS

| | | |
|---|---|---|
| EP | 299667 A1 | 1/1989 |
| EP | 1 034 734 A1 | 9/2000 |
| FR | 2686497 A1 | 7/1993 |
| WO | WO 88/02237 A1 | 4/1988 |
| WO | WO 89/05116 A1 | 6/1989 |
| WO | WO 94/01040 A1 | 1/1994 |
| WO | WO 94/13198 A1 | 6/1994 |
| WO | WO 94/24929 A1 | 11/1994 |

(Continued)

OTHER PUBLICATIONS

Bradburn, NM, et al. "Answering Autobiographical Questions: The Impact of Memory and Inference on Surveys" *Science* Apr. 10, 1987;236: 157–161.

Collins, RL, et al. "Ecological momentary assessment in a behavioral drinking moderation training program" *Exp. Clin. Psychopharmacol.* Aug. 1998;6(3):306–315.

Cramer, JA, et al. "How often is medication taken as prescribed?" *JAMA* Jun. 9, 1989;261(22):3273–3277.

(Continued)

*Primary Examiner*—George Davis
(74) *Attorney, Agent, or Firm*—Lahive & Cockfield, LLP

(57) ABSTRACT

A system for developing and implementing empirically derived algorithms to generate decision rules to predict subject noncompliance and fraud with research protocols in clinical trials allows for the identification of complex patterns of variables that detect or predict subject noncompliance and fraud with research protocol in the clinical trial. The present invention can also be used to monitor subject compliance with the research protocol to determine preferred actions to be performed. Optionally, the invention may provide a spectrum of noncompliance, from minor noncompliance needing only corrective feedback, to significant noncompliance requiring subject removal from the clinical trial. The algorithms and decision rules can also be domain-specific, such as detecting non-compliance or fraud among subjects in a cardiovascular drug trial, or demographically specific, such as taking into account gender or age which provides for algorithms and decision rules to be optimized for the specific sample of subjects being studied.

37 Claims, 2 Drawing Sheets

U.S. PATENT DOCUMENTS

| | | | | |
|---|---|---|---|---|
| 4,803,625 A | | 2/1989 | Fu et al. ................ | 364/413.03 |
| 4,844,076 A | | 7/1989 | Lesho et al. ................ | 128/631 |
| 4,883,063 A | | 11/1989 | Bernard et al. ............ | 128/670 |
| 4,909,260 A | | 3/1990 | Salem et al. ................ | 128/721 |
| 4,966,154 A | | 10/1990 | Cooper et al. .............. | 128/671 |
| 4,974,601 A | | 12/1990 | Tranjan et al. .............. | 128/696 |
| 4,975,842 A | | 12/1990 | Darrow et al. ......... | 364/413.02 |
| 4,987,897 A | | 1/1991 | Funke .................. | 128/419 PG |
| 5,002,064 A | | 3/1991 | Allain et al. ................ | 128/710 |
| 5,063,937 A | | 11/1991 | Ezenwa et al. ............. | 128/723 |
| 5,078,134 A | | 1/1992 | Heilman et al. ............ | 128/421 |
| 5,111,818 A | | 5/1992 | Suzuki et al. ............... | 128/644 |
| 5,113,859 A | | 5/1992 | Funke .................. | 128/419 PG |
| 5,128,552 A | | 7/1992 | Fang et al. ................... | 307/66 |
| 5,131,390 A | | 7/1992 | Sakaguchi et al. .......... | 128/632 |
| 5,137,345 A | | 8/1992 | Waldorf et al. ............. | 351/206 |
| 5,181,519 A | | 1/1993 | Bible ......................... | 128/704 |
| 5,197,489 A | | 3/1993 | Conlan ...................... | 128/782 |
| 5,199,439 A | | 4/1993 | Zimmerman et al. ....... | 128/670 |
| 5,213,106 A | | 5/1993 | Lerner ........................ | 128/698 |
| 5,213,555 A | | 5/1993 | Hood et al. ................... | 482/57 |
| 5,218,969 A | | 6/1993 | Bredesen et al. ........... | 128/710 |
| 5,222,503 A | | 6/1993 | Ives et al. ................... | 128/731 |
| 5,226,424 A | | 7/1993 | Bible ......................... | 128/696 |
| 5,226,539 A | | 7/1993 | Cheng ........................ | 206/534 |
| 5,228,450 A | | 7/1993 | Sellers ....................... | 128/711 |
| 5,253,654 A | | 10/1993 | Thomas et al. ............. | 128/779 |
| 5,261,412 A | | 11/1993 | Butterfield et al. ......... | 128/672 |
| 5,271,405 A | | 12/1993 | Boyer et al. ................ | 128/672 |
| 5,275,159 A | | 1/1994 | Griebel ....................... | 128/633 |
| 5,280,429 A | | 1/1994 | Withers ................ | 364/413.15 |
| 5,289,824 A | | 3/1994 | Mills et al. ................. | 128/696 |
| 5,307,263 A | | 4/1994 | Brown .................. | 364/413.09 |
| 5,447,164 A | | 9/1995 | Shaya et al. ................ | 128/710 |
| 5,454,376 A | | 10/1995 | Stephens et al. ............ | 128/721 |
| 5,583,831 A | | 12/1996 | Churchill et al. ............. | 368/10 |
| 5,596,994 A | | 1/1997 | Bro ............................ | 128/732 |
| 5,672,154 A | | 9/1997 | Sillén et al. ................... | 604/50 |
| 5,704,366 A | | 1/1998 | Tacklind et al. ............ | 128/716 |
| 5,710,551 A | | 1/1998 | Ridgeway .............. | 340/870.09 |
| 5,732,709 A | | 3/1998 | Tacklind et al. ............ | 128/726 |
| 5,778,882 A | | 7/1998 | Raymond et al. ........... | 128/700 |
| 5,832,448 A | | 11/1998 | Brown .......................... | 705/2 |
| 5,960,403 A | | 9/1999 | Brown .......................... | 705/2 |
| 5,963,136 A | | 10/1999 | O'Brien .................... | 340/573.1 |
| 6,039,688 A | | 3/2000 | Douglas et al. ............. | 600/300 |
| 6,063,028 A | * | 5/2000 | Luciano ...................... | 600/300 |
| 6,075,755 A | | 6/2000 | Zarchan ....................... | 368/10 |
| 6,095,985 A | | 8/2000 | Raymond et al. ........... | 600/513 |
| 6,151,586 A | | 11/2000 | Brown ......................... | 705/14 |
| 6,167,362 A | | 12/2000 | Brown et al. .................. | 703/11 |
| 6,317,731 B1 | * | 11/2001 | Luciano ....................... | 706/21 |
| 6,381,577 B1 | | 4/2002 | Brown .......................... | 705/2 |
| 2002/0019748 A1 | | 2/2002 | Brown .......................... | 705/2 |
| 2002/0042726 A1 | | 4/2002 | Brown .......................... | 705/2 |
| 2002/0052858 A1 | * | 5/2002 | Goldman et al. ............. | 706/15 |
| 2002/0064095 A1 | | 5/2002 | Momich et al. .............. | 368/10 |

FOREIGN PATENT DOCUMENTS

| | | |
|---|---|---|
| WO | WO 96/13790 A1 | 5/1996 |
| WO | WO 98/38909 A1 | 9/1998 |
| WO | WO 99/27483 A1 | 6/1999 |
| WO | WO 99/38052 A1 | 7/1999 |
| WO | WO 00/15103 A1 | 3/2000 |
| WO | WO 00/69331 A1 | 11/2000 |
| WO | WO 00/75748 A2 | 12/2000 |
| WO | WO 01/06433 A1 | 1/2001 |
| WO | WO 01/09701 A1 | 2/2001 |
| WO | WO 01/26020 A1 | 4/2001 |
| WO | WO 01/26021 A1 | 4/2001 |
| WO | WO 01/34024 A1 | 5/2001 |
| WO | WO 01/74229 A2 | 10/2001 |
| WO | WO 02/19247 A2 | 3/2002 |

OTHER PUBLICATIONS

Eich, E, et al. "Memory for Pain: Relation between Past and Present Pain Intensity" *Pain* 1985;23:375–380.

Friedman, WJ "Memory for the Time of Past Events" *Psychological Bulletin* 1993; 113(1):44–66.

Gorin, AA, et al. "Recall Biases and Cognitive Errors in Retrospective Self–Reports: A Call for Momentary Assessments" *Handbook of Heath Psychology.* Lawrence Erlbaum Assoc.:Mahwah, New Jersey. 2001;pp. 405–413.

Greeno, CG, et al. "Binge antecedents in obese women with and without binge eating disorder" *J. Consult Clin. Psychol.* Feb. 2000;68(1):95–102.

Hyland, ME, et al. "Diary keeping in asthma: comparison of written and electronic methods" *BMJ* Feb. 20, 1993;306(6876):487–489.

Kamarck, TW, et al. "The effects of psychosocial influences on ambulatory blood pressure: contrasting different measurement and data analytic strategies" 37th Annual Meeting of the Society for Psychophysical Research, N. Falmouth, Massachusetts, USA, Oct. 15–19, 1997. *Psychophysiology* 1997;34 (Suppl. 1):S6–S7.

Kamarck, TW, et al. "Effects of task strain, social conflict, and emotional activation on ambulatory cardiovascular activity: daily life consequences of recurring stress in a multiethnic adult sample" *Health Psychol.* Jan. 1998;17(1):17–29.

Kamarck, TW, et al. "Emotional Support Modrates The Acute Pressor Effects Of Stress During Daily Life" Abstracts of Papers for 1999 Annual Meeting: Paper Session: Cardiovascular Activity in Relation to Stress Psychology and Neurobiology. *Psychosomatic Medicine* 1999;61(1):112 (abstract).

Kamarck, TW, et al. "The Diary of Ambulatory Behavioral States: A new Approach to the Assessment of Psychosocial Influences on Ambulatory Cardiovascular Activity" *Technology and Methods in Behavioral Medicine* (D.S. Krantz and A. Baum, eds.) Lawrence Erlbaum Associates:Mahwah, New Jersey. 1998; Chapter 9:163–193.

O'Connell, KA, et al. "Overcoming the Urge to Smoke: The Strategies of Long–Term Abstainers and Later Relapsers" *Psychology of Addictive Behavior* 1991;5(1):1–8.

O'Connell, KA, et al. "Coping in real time: using Ecological Momentary Assessment techniques to assess coping with the urge to smoke" *Res. Nurs. Health.* Dec. 1998;21(6):487–497.

O'Connell, KA, et al. "Symptom beliefs and actual blood glucose in type II diabetes" *Res. Nurs. Health.* Jun. 1990;13(3):145–151.

O'Connell, KA, et al. "Reversal theory and smoking: a state–based approach to ex–smokers' highly tempting situations" *J. Consult. Clin. Psychol.* Aug. 1990;58(4):489–494.

O'Connell, KA "Why rational people do irrational things. The theory of psychological reversals" *J. Psychosoc. Nurs. Ment. Health Serv.* Jan. 1991;29(1):11–14.

Paty, J, et al. "The importance of assessing base rates for clinical studes: an example of stimulus control of smoking" *The Experience of Psychopathology: Investigating Mental Disorders in their Natural Settings* (DeVries, Marten W. ed.) Cambridge University Press:Cambride, England. 1992; pp. 347–352.

Penner, LA, et al. "Individual Differences in Intraperson Variability in Mood" *Journal of Personality and Social Psychology* 1994;66(4):712–721.

Potocky, M, et al. "State–outcome consistency in smoking relapse crises: a reversal theory approach" *J. Consult. Clin. Psychol.* Apr. 1991; 59(2):351–353.

Raynor, DA, et al. "The effects of social influence on cardiovascular responsiveness in the natural environment" 37th Annual Meeting of the Society for Psychophysical Research, N. Falmouth, Massachusetts, USA, Oct. 15–19, 1997. *Psychophysiology* 1997;34 (Suppl. 1):S73.

Ross, M "Relation of Implicit Theories to the Construction of Personal Histories" *Psychological Review* 1989;96(2):341–357.

Schwartz, JE, et al. "Does trait coping exist? A momentary assessment approach to the evaluation of traits" *J. Pers. Soc. Psychol.* Aug. 1999; 77(2):360–369.

Schwartz, JE, et al. "Strategies for analyzing ecological momentary assessment data" *Health Psychol.* Jan. 1998;17(1):6–16.

Shiffman, S. "Real–Time Self–Report of Momentary States in the Natural Environment: Computerized Ecological Momentary Assessment" *The Science of Self–Report: Implicates for Research and Practice* (A. Stone, et al. eds.) Lawrence Erlbaum Associates:Mahwah, New Jersey. 1989; Chapter 16: 277–296.

Shiffman, S. "Assessing Smoking Patterns and Motives" *Journal of Consulting and Clinical Psychology* 1993;61(5):732–742.

Shiffman, S, et al. "Drinking and Smoking: A Field Study of their Association" *Annals of Behavioral Medicine* 1994;16(3):203–209.

Shiffman, S, et al. "Nicotine withdrawal in chippers and regular smokers: subjective and cognitive effects" *Health Psychol.* Jul. 1995;14(4):301–309.

Shiffman, S, et al. "First lapses to smoking: within–subjects analysis of real–time reports" *J. Consult. Clin. Psychol.* Apr. 1996;64(2):366–379.

Shiffman, S, et al. "Progression from a smoking lapse to relapse: prediction from abstinence violation effects, nicotine dependence, and lapse characteristics" *J. Consult. Clin. Psychol.* Oct. 1996;64(5):993–1002.

Shiffman, S, et al. "Temptations to smoke after quitting: a comparison of lapsers and maintainers" *Health Psychol.* Nov. 1996;15(6):455–461.

Shiffman, S, et al. "A day at a time: predicting smoking lapse from daily urge" *J. Abnorm. Psychol.* Feb. 1997;106(1):104–116.

Shiffman, S, et al. "Remember that? A comparison of real–time versus retrospective recall of smoking lapses" *J. Consult. Clin. Psychol.* Apr. 1997;65(2):292–300.

Shiffman, S, et al. "Individual differences in the context of smoking lapse episodes" *Addict. Behav.* Nov.–Dec. 1997;22(6):797–811.

Shiffman, S, et al. "The Abstinence Violation Effect Following Smoking Lapses and Temptations" *Cognitive Therapy and Research* 1997;21(5):497–523.

Shiffman, S, et al. "The effect of bupropion on nicotine craving and withdrawal" *Psychopharmacology* Jan. 2000;148(1):33–40.

Shiffman, S, et al. "Dynamic effects of self–efficacy on smoking lapse and relapse" *Health Psychol.* Jul. 2000;19(4):315–323.

Shiffman, S, et al. "Comparative efficacy of 24–hour transdermal nicotine patches for relief of morning craving" *Addiction* Aug. 2000;95(8): 1185–1195.

Stone, AA, et al. "Ecological Momentary Assessment (EMA) in Behavioral Medicine" *Annals of Behavioral Medicine* 1994;16(3):199–202.

Stone, AA, et al. "A comparison of coping assessed by ecological momentary assessment and retrospective recall" *J. Pers. Soc. Psychol.* Jun. 1998;74(6):1670–1680.

Stone, AA, et al. "Ecological Momentary Assessment" *Well-–being: The foundations of Hedonic psychology.* Kahneman, Daniel et al. (eds.). Russell Sage Foundation: New York, NY. 1999;pp. 26–39.

Stone, AA, et al. "Does the peak–end phenomenon observed in laboratory pain studies apply to real–world pain in rheumatoid arthritics?" *The Journal of Pain* Fall 2000;1(3):212–217.

Straka, RJ, et al. "Patient and self–reporting of compliance does not correspond with electronic monitoring: an evaluation using isosorbide dinitrate as a model drug" *Pharmacotherapy* 1997 Jan.–Feb. 1997;17(1):126–132.

Wiesspeiner, G, et al. "Multichannel Ambulatory Monitoring of Circulation Related Biosignals" *Proceedings. Computers in Cardiology,* Sep. 23–26, 1991, Venice, Italy. IEEE Comput. Soc. Press: Los Alamitos, CA, USA. 1991;p. 457–460.

Powell, JH "Handhelds aid doctors" Retrieved from the Internet, www.bostonherald.com/business/technology/palm07032000.htm Jul. 3, 2000.

Salford Systems "CART® for Windows User's Guide. A Salford Systems Implementation of the Original CART Program" 1999;i–v, 1–90, Index.

Tomkies, KK "Taking a New Tack on Clinical Trial Data Collecion: New Internet–based software aims to improve data integrity, helping speed data transmission in the process" Retrieved from the Internet www.office.com/global/0,,53–17789,FF.html May 18, 2000.

* cited by examiner

APPARATUS AND METHOD FOR PREDICTION AND MANAGEMENT OF SUBJECT COMPLIANCE IN CLINICAL RESEARCH

REFERENCE TO RELATED APPLICATIONS

The subject matter of this application relates to the patent application titled "System for Clinical Trial Subject Compliance", Ser. No. 09/825,533, and filed on even date herewith. The aforementioned application, and the references cited therein, are incorporated herein by reference.

FIELD OF THE INVENTION

The present invention relates to predicting subject behavior during research, especially clinical trials. Specifically, the invention relates to the prediction of subject noncompliance with protocols in clinical trials.

BACKGROUND OF THE INVENTION

Evaluation of subject compliance with research protocols typically looks at only one variable at a time. Such evaluation is not empirically derived by quantitative analysis of existing datasets, instead relying on the researcher's judgment and biases to determine whether and what type of corrective action is required. Furthermore, evaluation of subject compliance with clinical trial protocols has typically not taken into account the domain of the clinical trial or the characteristics of the subjects. Finally, such evaluation often cannot be made in a timely way, but is made only after serious noncompliance has already occurred.

SUMMARY OF THE INVENTION

The goal of clinical trials is to collect valid, reliable data on one or more conditions within a clinical trial group of subjects. Subjects in clinical trials are assigned tasks related to treatment and data collection in accordance with a research protocol. The integrity of clinical trials rests upon subjects' faithful performance of these tasks. If subjects fail to comply with the protocol, the trial fails to yield reliable, valid results. Thus, subject noncompliance in clinical trials is a significant risk and cost to the pharmaceutical industry. Accordingly, predicting subject performance and assessment of such performance is of substantial value to clinical research.

The benefits of a system that can predict and track subject compliance in a clinical trial include: reliable, valid data; increased statistical power; reduced clinical trial costs through smaller sample sizes; reduced time to complete the clinical trial; and, ultimately, reduced time to get a drug or medical device to market.

According to one embodiment of the invention, a method of predicting subject noncompliance is provided. The method includes the steps of providing historical subject compliance data, generating at least one predictive algorithm for predicting subject noncompliance by quantitative analysis of the historical subject compliance data, and translating the at least one predictive algorithm into at least one prediction rule for use with a clinical trial.

According to another embodiment, a method of determining subject noncompliance includes the steps of providing at least one of the group of historical subject compliance data and historical protocol data and generating at least one algorithm reflective of at least one of historical subject compliance data and historical protocol data by quantitatively analyzing the historical subject compliance data and the historical protocol data. The method also includes translating the algorithm into at least one decision rule for analyzing subject compliance information, obtaining the subject compliance information and comparing the subject compliance information to the at least one decision rule to determine if corrective action is needed.

According to a further embodiment, a method of the invention includes the steps of providing historical subject compliance data and historical protocol data, generating a spectrum of noncompliance representative of the historical subject compliance data not compliant with the historical protocol data by quantitative analysis of the historical subject compliance data and the historical protocol data, obtaining subject compliance information and comparing the spectrum of noncompliance to the subject compliance information to determine if corrective action is needed.

According to an embodiment of the invention a method of detecting subject fraud is provided, having the steps of providing historical subject compliance data and historical protocol data, generating at least one fraud detection algorithm for detecting subject fraud by quantitative analysis of the historical subject compliance data and the historical protocol data and translating the at least one fraud detection algorithm into at least one fraud detection rule for use with a clinical trial.

According to an embodiment of the invention another method of detecting subject fraud is provided, having the steps of providing subject compliance data, generating at least one fraud detection algorithm for detecting subject fraud by quantitative analysis of the compliance data and translating the at least one fraud detection algorithm into at least one fraud detection rule for use with a clinical trial.

According to an embodiment of the invention a medium suitable for use in an electronic device and having instructions for execution on the electronic device, the instructions, having the steps of providing at least one of the group of historical subject compliance data and historical protocol data, generating at least one predictive algorithm for predicting subject noncompliance by quantitative analysis of at least one of the group of the historical subject compliance data and the historical protocol data and translating the at least one predictive algorithm into at least one prediction rule for use with a clinical trial.

According to another embodiment of the invention a medium suitable for use in an electronic device and having instructions for execution on the electronic device, the instructions having the steps of providing at least one of the group of historical subject compliance data and historical protocol data, generating at least one algorithm reflective of at least one of the group of the historical subject compliance data and the historical protocol data by quantitative analysis of the historical subject compliance data and the historical protocol data, translating the at least one algorithm into at least one decision rule for analyzing subject compliance information, obtaining the subject compliance information and comparing the subject compliance information to the at least one decision rule to determine if corrective action is needed.

According to another embodiment of the invention a medium suitable for use in an electronic device and having instructions for execution on the electronic device, the instructions having the steps of providing historical subject compliance data and historical protocol data, generating a spectrum of noncompliance representative of the historical subject compliance data not compliant with the historical protocol data by quantitative analysis of the historical subject compliance data and the historical protocol data, obtaining subject compliance information and comparing the spectrum of noncompliance to the subject compliance information to determine if corrective action is needed.

According to a further embodiment of the invention a medium suitable for use in an electronic device and having instructions for execution on the electronic device, the instructions having the steps of providing historical subject compliance data and historical protocol data, generating at least one fraud detection algorithm for detecting subject fraud by quantitative analysis of the historical subject compliance data and the historical protocol data and translating the at least one fraud detection algorithm into at least one fraud detection rule for use with a clinical trial.

According to an embodiment of the invention a medium suitable for use in an electronic device and having instructions for execution on the electronic device, the instructions having the steps of providing subject compliance data, generating at least one fraud detection algorithm for detecting subject fraud by quantitative analysis of the compliance data and translating the at least one fraud detection algorithm into at least one fraud detection rule for use with a clinical trial.

BRIEF DESCRIPTION OF THE DRAWINGS

The foregoing and other objects, features and advantages of the invention will be apparent from the following description and apparent from the accompanying drawings.

DETAILED DESCRIPTION OF THE INVENTION

Figure 1:
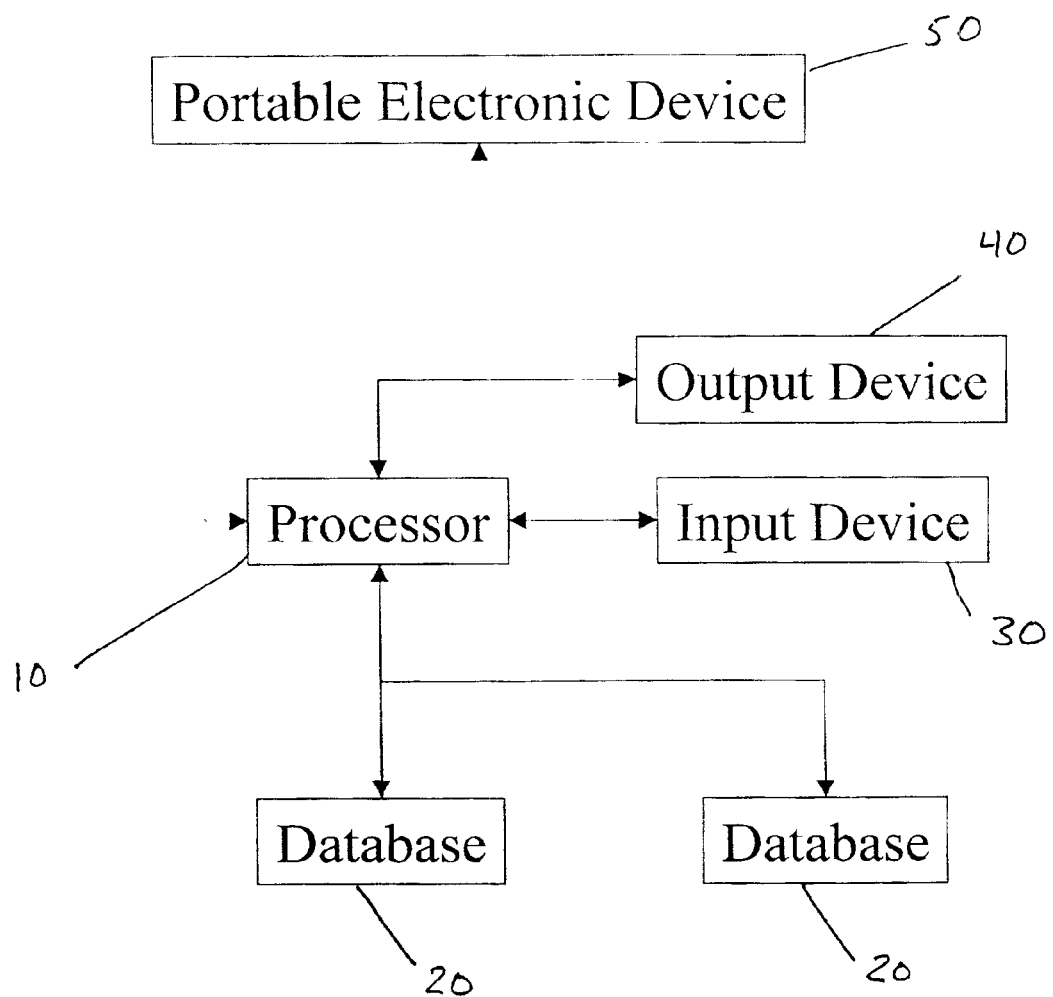
FIG. 1 illustrates a system for determining subject noncompliance according to the teachings of the present invention.

The present invention involves an empirically derived set of algorithms and decision rules to predict subject compliance, and detect noncompliance, with research protocols. The present invention uses algorithms and decision rules to provide an empirical approach for predicting different types of subject noncompliance with research protocols. This actuarial approach to predicting subject noncompliance with clinical trial protocols is consistent with empirical research demonstrating the superiority of actuarial prediction of human behavior as compared to subjective clinical judgment. According to an alternative embodiment of the invention, a portable electronic device is used to query and collect data from the subject.

As used herein "clinical trial" refers to a broad range of data collecting activities, including studies directed to monitoring of one or more conditions within a clinical trial group of subjects. One such example includes drug trials involving humans. As used herein "subject" refers to any participant in a clinical trial, whether or not the subject has any relationship to a doctor or other medical professional.

"Trial data" or "clinical trial data" refers to data gathered for the principle purpose of the clinical trial. For example, trial data would include pain levels experienced by subjects in a pain medication clinical trial or craving levels in an anti-smoking medication clinical trial.

"Evaluability data" or "compliance data" or "compliance information" is data that relates to the circumstances under which the trial data was collected or other data pertaining to characteristics of the trial data or other evaluability data. Some examples include timeliness, consistency with other collected data, proximity of the data to an expected data range and completeness of the data.

"Historical protocol data" includes data specifying the research protocol of earlier clinical trials. Examples of historical protocol data can include questions posed to subjects, frequency of prompting of a subject during various times of the day or week, time allowed for subjects to respond to questions, requirements of subject behavior, and conditions mandating removal of a subject from certain statistical analyses or removal as participant in the clinical trial.

As used herein "portable electronic device" refers to any electronic device that can be adapted for use by a subject and/or clinical staff for viewing and/or inputting information. Preferably, the portable electronic device will also have a visual, audible or tactile alarm to gain the attention of the subject. For example, a pager having a vibration alarm may be used as a portable electronic device. Further examples include, pagers with audible alarms and/or text messaging capabilities, a laptop computer or a cell phone. Preferably, according to the invention, a portable electronic device will be a handheld computer provided with a display and a data input feature, such as a touch-sensitive screen, or buttons to enable a subject to respond to questions posed on the display or to input unsolicited information. Examples of such portable electronic devices include the Palm Pilot by Palm, Inc or Windows-based devices running Pocket PC from Microsoft Corporation. Preferably, the portable electronic device will also be adapted to communicate with at least one other computer via a wireless connection or via a wired connection, including the use of a modem and/or a network, such as a LAN or the Internet.

According to an embodiment of the present invention, a system is provided as shown in FIG. 1. A processor 10 is provided and is adapted to communicate with at least one database 20. As discussed below, the database preferably stores data related to subject compliance and associated research protocols. An input device 30 is also provided to allow the subject or another person to provide input to the processor 10. The input device 30 may be a keyboard, a modem or other such device adapted for communication with the processor. An output device 40 is also preferably provided to receive and display information from the processor 10. Examples of output devices 40 include a printer and a monitor.

In one embodiment of the invention, a portable electronic device 50 is provided and is selectively operatively coupled to the processor 10. The portable electronic device 50 can also include a processor and may serve as an alarm, an input device, an output device, and/or a database. One example of a portable electronic device is a Palm Pilot by Palm, Inc, as described above.

Figure 2:
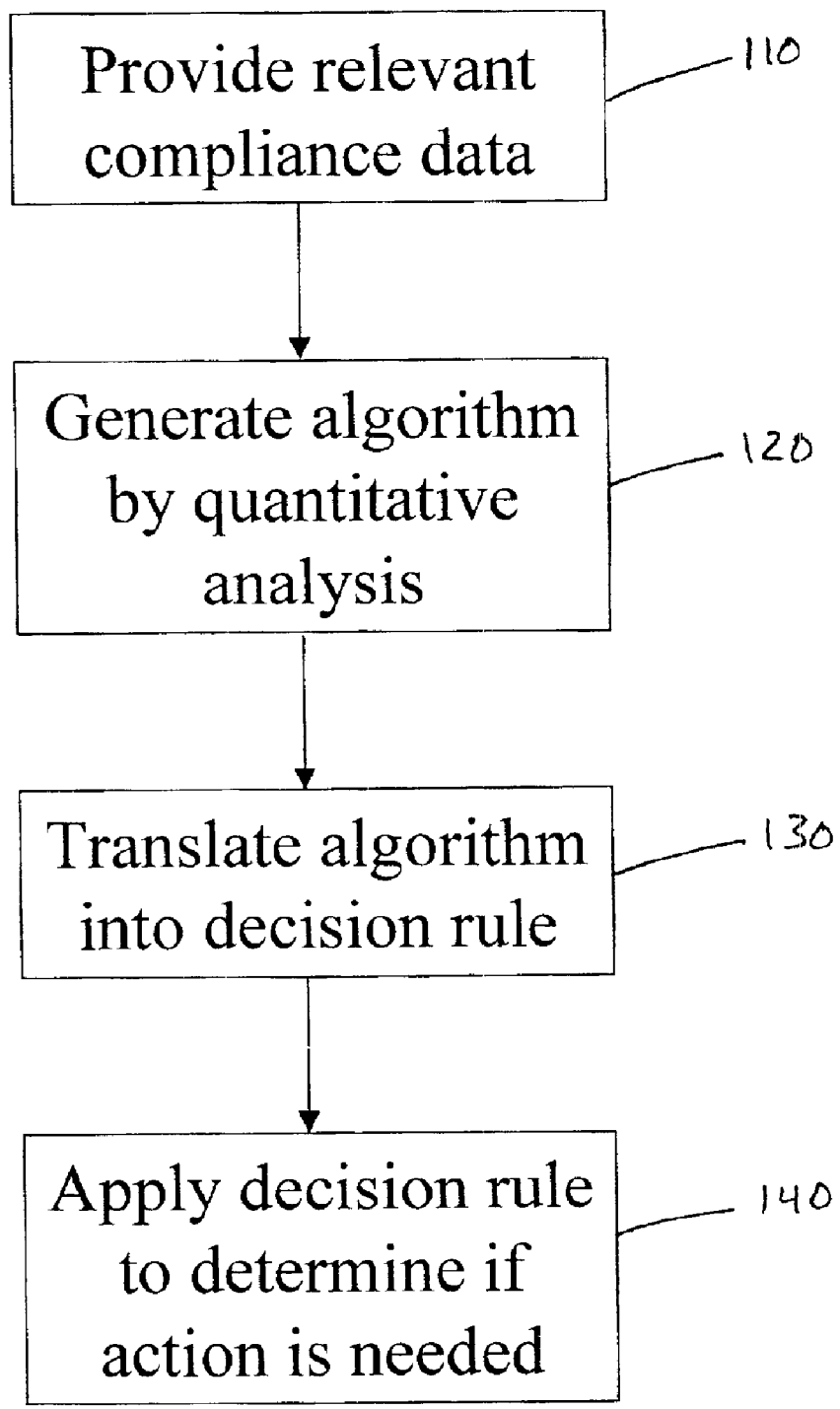
FIG. 2 is a schematic flow chart diagram illustrating the method according to the teachings of the present invention.

According to an embodiment of the invention, a flow chart illustrating the method of the present invention is set forth in FIG. 2. First, relevant subject compliance data, and associated protocol data, reflecting subject compliance with research protocols in clinical trials, is provided, step 110. Optionally, only subject compliance data may be provided, as some application of the present invention may not require knowledge of associated historical protocol for use of the subject compliance data. For example, analysis of response times to questions may not require knowledge of the maximum permissible time for subjects to answer questions in earlier clinical trials.

Subject compliance data and associated protocol data is preferably stored in one or more databases 20 and may be identified from earlier clinical trials and/or earlier activities of a current clinical trial. An output of the present invention preferably includes a database to provide subject compliance data and associated protocol data for later use by the invention.

The subject compliance data and associated protocol data is preferably specific to the type of condition or medication that is the focus of the clinical trial. For example, if the clinical trial relates to a cardiovascular condition, the data preferably relates to subject compliance with protocols in cardiovascular clinical trials. Likewise, if the clinical trial relates to a cardiovascular medication, the data used in the present invention will preferably relate to subject compliance with protocols in cardiovascular clinical trials. It is also within the scope of the invention to optionally include subject compliance data and associated protocol data obtained from an earlier phase of the clinical trial into the compliance data of the present invention. Alternatively, the subject compliance data and associated protocol data may not be related to the type of condition or medication that is the focus of the clinical trial.

Next, at least one algorithm representative of the subject compliance data is generated by quantitative analysis of the compliance data, step 120. Preferably, multiple algorithms are generated. The present invention involves the application of statistical and other quantitative methods to screen existing research data for markers of, e.g. variables related to, noncompliance with research protocols. Preferably, the subject compliance data is also reviewed to exclude invalid data. For example, data reported by one subject that appears to be well outside a range established by all other subjects can indicate invalid data.

Examples of various types of data that may be collected according to an embodiment of the invention include variables that may represent 'non-intuitive' predictors such as: gender of the subject, disease severity, the time of the year, and the day of the week.

Quantitative analysis methods are used to distinguish, identify, and predict instances of good and poor compliance and/or instances of valid or invalid data entries. The quantitative analysis methods of the present invention may include, but are not limited to, application of a variety of statistical and data mining techniques, such as logistic regression, discriminant function analysis, classification and regression trees, neural networks, and multiple linear regression to screen existing data and derive algorithms to identify markers of noncompliance with research protocols.

Logistic regression analyses use dichotomous and continuous variables to predict dichotomous outcome variables. For example, dichotomous outcome variables can indicate "completed" or "failed to complete" a clinical trial monitoring protocol. Discriminant function analysis relates a categorical criterion variable to dichotomous or linear predictors. Classification and Regression Trees (CART) use binary recursive partitioning to identify unique groups of subjects, such as, for example, subjects failing to complete the clinical trial protocol and subjects completing the protocol with minimal corrective feedback regarding their compliance with the clinical trial protocol. Neural network approaches to pattern recognition examine data for patterns and classify certain patterns of data based on the probability that they lead to a given outcome. Multivariate Regressive Splines (MARS) build flexible regression models, including interactions, by fitting separate splines to distinct intervals of the predictor variables.

Other nonparametric and parametric statistical approaches can also be applied to the prediction of subject noncompliance with clinical trial protocols.

A variety of predictor and criterion variables can be used in the present invention. Predictor variables can range between basic demographic characteristics, such as, for example, gender, to specific clinical trial compliance related variables, such as, for example, mean latency to respond to an audible prompt from an optional portable electronic device. Similarly, criterion variables can range from subtle, such as, for example, missing some percentage of portable electronic device prompts, to severe noncompliance, such as, for example, failure to complete the clinical trial protocol. For detection of fraudulent entries, example predictor variables could include the speed or rate of entries, or an implausible or statistically unlikely pattern of answers to a set of assessment questions.

The present invention allows for complex, non-intuitive interactions among multiple variables to optimally predict subject compliance with clinical trial protocols. That is, the markers or variables used to predict noncompliance may or may not, in and of themselves, be related to noncompliance. Algorithms may rely on different variables for different subgroups. For example, subgroups can include, but are not limited to, men and women, older or younger subjects, or subjects late or early in the clinical trial. The algorithms may also identify different combinations of variables working only in tandem. Thus, the variables alone may not be directly, simply, or obviously related to noncompliance. The algorithms of the invention may use complex and nonintuitive combinations of predictors to predict subject noncompliance with clinical trial protocols.

The invention also allows context-specific algorithms to maximize predictive utility. That is, different algorithms can be derived for different groups of subjects, such as, for example, subjects with cardiovascular or central nervous system diseases. As a result, the present invention avoids assuming that any given set of variables will be equally predictive of clinical trial noncompliance for all types of conditions or diseases or for all types of subjects.

According to an embodiment of the invention, the present invention also provides for novel quantitative analyses to be incorporated into the development of algorithms to further improve their predictive validity. Specifically, the algorithms can be subject to continuous improvement as more data become available for analysis, either within an individual clinical trial or accumulating across clinical trials.

According to a further embodiment of the invention, algorithms can be used to determine appropriate feedback to both subjects and research staff regarding compliance with the protocol. For example, a computer program can implement decision rules based on these algorithms, and automatically determine appropriate feedback or action by the personnel involved in conducting the clinical trial.

An advantage of the present invention is that, because the algorithms and decisions are based on formal, empirical, and quantitative criteria, they remove the subjective element in these decisions, which in turn minimizes the potential for bias.

The above and other advantages provided by the disclosed invention include provisions for the application of these algorithms within existing and yet to be developed processes for giving systematic feedback to subjects, research sites, and clinical trial sponsors conducting clinical trials using clinical trials.

Once the one or more algorithms of the invention have been derived from analysis of existing data, the algorithms can be translated into specific decision rules, step 130. Decision rules are essentially reformatted algorithms that can be applied to current subject compliance data to determine whether action is needed, step 140. Decision rules may determine a threshold of compliance or a threshold of noncompliance. Optionally, a decision rule may identify a spectrum of noncompliance, from minor noncompliance needing only corrective feedback, to significant noncompliance requiring subject removal from the clinical trial. Decision rules may be based on the specific dependent variable used to derive the algorithm or may be based on one or more differing variables.

For example, a subject who, within the first two days of the clinical trial, does not respond to more than 20% of prompted inquiries and either suspends prompting more than once or indicates he/she is napping more than once may be identified as failing to comply with the research protocol. As another example, subjects who suspend prompting at least twice, and whose total time of such suspension exceeds 2 hours, might be determined to be likely noncompliant, regardless of their overall performance. For purposes of illustration, one sample decision rule may be stated as:

Display noncompliance remediation message to clinical staff if:

[0.32(ratio of missed random prompts)+0.45(mean number of minutes spent time delaying assessments per day/100)+0.80(mean number of hours spent in sleep each night over past 7 days/10)]>1 where if noncompliance is determined by this decision rule, an action, such as sending a specific message to the clinical staff is recommended. For example, in the present example, the message "Subject is not following the protocol as required, resulting in substantial missed assessments. Call subject." may be determined to be the appropriate action.

According to an embodiment of the invention, criteria for identifying a subject as noncompliant with the research protocol need not overlap with criteria developed for determining whether to drop a subject from the clinical trial or exclude data related to that subject from the clinical trial results. For example, the decision rule(s) related to dropping a subject from the clinical trial might be based on failed responses to audible prompts rather than on suspension of prompting.

Typically, a decision rule specifies what type of action is required and may provide specific action details. Action types include corrective, affirmative and anti-fraud actions. Action details may include the content of a message to be provided to a subject or to clinical staff.

Decision rules may be translated from algorithms that identify patterns of noncompliance data that are harbingers or leading indicators of later, more serious, noncompliance. This would allow early action to be taken based on these indicators. Such decision rules would typically be in the form of contingencies or conditions based on early compliance indicators.

Optionally, translation of algorithms to decision rules may involve human input or additional factors. For example, balancing the impact of a decision rule against the focus of the clinical trial may result in an alteration of the decision rule. For example, if subjects' heart rates are being monitored, frequency of prompting or loudness of reminder alerts may be minimized so as not to artificially raise subject heart rates. Also, clinical staff may alter decision rules based on their assessment of external factors outside of the scope of the quantitative analysis. An example may include providing more alerts to clinical staff instead of directly to subjects to provide more interaction between clinical staff and the subjects.

A decision rule may also be used to predict which subjects will fail to complete a clinical trial protocol. Therefore, a decision to rule to drop the subject from the clinical trial, or to work to improve subject performance, can be made at an early time. By providing those conducting a clinical trial with early feedback regarding subject noncompliance with a research protocol, the present invention improves clinical trial data quality and may potentially save both time and money by either improving the compliance of potentially noncompliant subjects or excluding unimprovable noncompliant subjects early in a clinical trial.

The generation of a fraud detection algorithm can take many forms. The psychometric properties of the scale itself could be used to identify potentially fraudulent responses. For example, according to one embodiment of the invention, item response theory uses known properties of individual items within an assessment to estimate the probability that an observed pattern of responses is valid. Therefore, a subject answering yes to the question "My headaches are completely debilitating" has a low probability of also answering yes to the question "My headaches are a minor inconvenience" such that observing this pattern of responses could be indicative of fraud.

According to a further embodiment of the invention, the detection of fraudulent or invalid entries in subject-supplied data may be performed similarly to the methods described herein. For example, the analysis could be based on statistical properties of the responses themselves. Thus, as an example, analysis might indicate that when the standard deviation across subject responses on a particular questionnaire are less than 1.0, fraudulent or invalid completion is highly likely.

The content of subjects' responses could optionally be used as a source of data for the fraud detection algorithms if the responses are invariant or relatively invariant. For example, a subject answering 'yes' to all questions, even when the logical content of the questions would suggest some alternating pattern of appropriate responses.

Analysis of fraud could also be based on particular combinations of responses. Thus, subjects who answered that they took pain medication five or more times daily, but who elsewhere indicated either that pain severity was 4, on a scale of 1 to 10, or that pain frequency was 'infrequent' or 'rare', might be flagged as cases likely to be invalid. The response patterns determined to represent potentially fraudulent data need not be logically inconsistent or intuitively invalid. Rather, they are determined to represent potentially fraudulent data based on statistical analysis comparing valid and invalid response profiles. Therefore, questions posed to subjects can be tailored to provide opportunities for the subject to contradict, or appear in disagreement with, responses to earlier questions.

In an alternative embodiment, the posing of questions providing opportunities to contradict earlier responses can be interactive. For example, further questions providing opportunities to contradict earlier responses can be posed only if a response to a question appears unusual or if a decision rule indicates earlier indications of potential fraud.

As a further example, the time required for a subject to respond to items could be the foundation for the generation of fraud detection algorithms. For example, evaluability data could be used to estimate the mean length of time subjects take to respond to certain items. In such an example, response latencies less than two standard deviations below those norms could be the basis of identifying the responses as potentially fraudulent. For example, if a question contains 25 words and subjects take an average of 8 seconds to answer the question, responses of less than 1 second could be identified as potentially fraudulent.

Alternatively, the portable electronic device could capture certain ecological data such as temperature or airborne particles, or physiological data, such as concurrent heart rate, suggestive of a particular location, subjective, or physical state, which is inconsistent with the subject's responses, suggesting possible fraud.

In an alternative embodiment of the invention, subjects can be included in the clinical trial for the purpose of providing fraudulent data. For example, in a group of 100 subjects, 20 subjects may be asked to provide fraudulent data. By having such fraudulent data among data provided by the subjects, the quantitative analysis of the present invention can be used to ensure the resulting algorithms and decision rules detect the known fraudulent entries. In the event other subjects are also fraudulently recording data without the knowledge of the clinical staff, the algorithms and decision rules will likely also detect such unknown fraudulent activity.

Each of the above variations for detection of fraud can be used according to various embodiment of the present invention individually, sequentially or in combination.

According to a preferred embodiment of the invention, the system of the invention for automated processing of data collected via a portable electronic device is provided. In this embodiment, the portable electronic device or system is designed to prompt a subject for information and/or collect information as recorded by the subject without prompting. Preferably, each subject in the clinical trial is provided with a portable electronic device. The portable electronic device is preferably used to collect compliance-relevant variables, such as the number of data entry episodes, missed data entry occasions (e.g., instances where the portable electronic device prompts for data, but the subject fails to respond). A database of these variables is preferably processed according to the decision rules to guide the actions of the portable electronic device as described in detail in the copending patent application titled "System for Clinical Trial Subject Compliance", Attorney Docket No. IVQ-002.

The portable electronic device is also preferably adapted to communicate with another computer to allow the clinical staff to consolidate the data from all subjects in the clinical trial into one location for review or processing. Preferably, the portable electronic device will also be adapted to communicate with at least one other computer via a wireless connection or via a wired connection, including the use of a modem and/or a network, such as a LAN or the Internet. For example, by the use of the Internet or a dial-up modem connection, a subject may submit information from the portable electronic device to the clinical staff from the subject's home.

In another embodiment, a portable electronic device or a computer is adapted to communicate with clinical trial equipment used for measuring, monitoring, controlling or recording data or a process of the clinical trial. Examples of such processes include administration of medication or monitoring of heart rates. The portable electronic device or a computer preferably automatically records desired data for incorporation in the clinical trial data or compliance data.

In another embodiment of the invention, a paper form, such as a case report form, can be used by the subject to record data. The data can then be entered into a database by the use of a portable electronic device or other computer at an appropriate time. Examples of case report forms include hand-written forms and forms that allow for machine readable marks to be made, enabling automated scanning of the case report forms during entry of the data into a computer.

In an alternative embodiment of the present invention, the methods of the present invention may be incorporated in instructions recorded on a medium suitable for use in an electronic device, such as a computer, computer network server or a portable electronic device. The medium can include, for example, a hard disk, RAM medium, diskette, CD-ROM or other optical or magnetic storage medium. The instructions can optionally be stored on a server that can be remote from the subject or clinical staff member.

According to an embodiment of the invention, the server can provide data to be displayed. Data may be displayed at the server itself or be transmitted to another location, such as via hardwired or wireless access to the server, including a LAN or the Internet. The data can be processed to provide a graphical display to interested parties. Examples of those who may be interested in viewing the graphical representation of the compliance data include a site coordinator (who may be interacting with the subject), a clinical research organization (who may be responsible for study execution across a number of research locations), other agencies interested in the collection of the data, or the sponsor of the research.

According to another embodiment of the invention, the server can provide ongoing aggregation of data across subjects to speed the time required to combine, clean, and make available final data.

These examples are meant to be illustrative and not limiting. The present invention has been described by way of example, and modifications and variations of the exemplary embodiments will suggest themselves to skilled artisans in this field without departing from the spirit of the invention. Features and characteristics of the above-described embodiments may be used in combination. The preferred embodiments are merely illustrative and should not be considered restrictive in any way. The scope of the invention is to be measured by the appended claims, rather than the preceding description, and all variations and equivalents that fall within the range of the claims are intended to be embraced therein.

Having described the invention, what is claimed as new and protected by Letters Patent is:

1. A method of predicting subject noncompliance, comprising the steps of:
   providing historical subject compliance data;
   generating at least one predictive algorithm for predicting subject noncompliance by quantitative analysis of the historical subject compliance; and
   translating the at least one predictive algorithm into at least one prediction rule for use with a clinical trial.

2. The method of predicting subject noncompliance of claim 1, further comprising the steps of:
   obtaining subject compliance information; and
   comparing the subject compliance information to the at least one prediction rule to determine if action is needed.

3. The method of predicting subject noncompliance of claim 2, further comprising the step of determining an appropriate action if the step of comparing indicates that action is needed.

4. The method of predicting subject noncompliance of claim 2, wherein the step of obtaining includes the step of employing a portable electronic device capable of displaying information and receiving and storing input from a user.

5. The method of predicting subject noncompliance of claim 2, further comprising the step of creating an evaluability database adapted to store data related to subject compliance.

6. The method of predicting subject noncompliance of claim 5, wherein the evaluability database is tailored to a condition affecting the subject.

7. The method of predicting subject noncompliance of claim 1, wherein said step of providing includes providing historical protocol data and wherein said step of generating includes quantitative analysis of the historical protocol data.

8. The method of determining subject noncompliance of claim 1, wherein the step of providing employs at least one database containing at least one of the group of the historical subject compliance data and the historical protocol data.

9. A method of determining subject noncompliance, comprising the steps of:
   providing at least one of the group of historical subject compliance data and historical protocol data;
   generating at least one algorithm reflective of at least one of the group of the historical subject compliance data and the historical protocol data by quantitative analysis of the historical subject compliance data and the historical protocol data;
   translating the at least one algorithm into at least one decision rule for analyzing subject compliance information;
   obtaining the subject compliance information; and
   comparing the subject compliance information to the at least one decision rule to determine if corrective action is needed.

10. The method of determining subject noncompliance of claim 9, further comprising the step of determining an appropriate corrective action if the step of comparing indicates that corrective action is needed.

11. The method of determining subject noncompliance of claim 9, wherein the step of obtaining includes using a portable electronic device capable of displaying information and receiving and storing input from a user.

12. The method of determining subject noncompliance of claim 9, wherein the step of generating employs at least one of the group of multiple linear regression, discriminant function analysis, logistic regression, neural networks, classification trees and regression trees.

13. The method of determining subject noncompliance of claim 9, wherein the step of providing employs at least one database containing at least one of the group of the historical subject compliance data and the historical protocol data.

14. A method of determining subject noncompliance, comprising the steps of:
   providing historical subject compliance data and historical protocol data;
   generating a spectrum of noncompliance representative of the historical subject compliance data not compliant with the historical protocol data by quantitative analysis of the historical subject compliance data and the historical protocol data;
   obtaining subject compliance information; and
   comparing the spectrum of noncompliance to the subject compliance information to determine if corrective action is needed.

15. The method of determining subject noncompliance of claim 14, further comprising the step of determining an appropriate corrective action if the step of comparing indicates that corrective action is needed.

16. The method of determining subject noncompliance of claim 15, wherein the step of obtaining includes using a portable electronic device capable of displaying information and receiving and storing input from a user.

17. A method of detecting subject fraud, comprising the steps of:
   providing historical subject compliance data and historical protocol data;
   generating at least one fraud detection algorithm for detecting subject fraud by quantitative analysis of the historical subject compliance data and the historical protocol data; and
   translating the at least one fraud detection algorithm into at least one fraud detection rule for use with a clinical trial.

18. A method of detecting subject fraud, comprising the steps of:
   providing subject compliance data;
   generating at least one fraud detection algorithm for detecting subject fraud by quantitative analysis of the compliance data; and
   translating the at least one fraud detection algorithm into at least one fraud detection rule for use with a clinical trial.

19. The method of detecting subject fraud of claim 18, further comprising the steps of:
   comparing the subject compliance information to the at least one fraud detection rule to determine if action is needed.

20. The method of detecting subject fraud of claim 19, further comprising the step of determining an appropriate action if the step of comparing indicates that action is needed.

21. The method of detecting subject fraud of claim 19, wherein the step of providing includes the use of a portable electronic device capable of displaying information and receiving and storing input from a user.

22. The method of detecting subject fraud of claim 19, further comprising the step of creating an evaluability database adapted to store data related to subject fraud.

23. The method of detecting subject fraud of claim 22, wherein the evaluability database is tailored to a condition affecting the subject.

24. The method of detecting subject fraud of claim 18, wherein the step of providing employs at least one database containing at least one of the group of the historical subject compliance data and the historical protocol data.

25. A medium suitable for use in an electronic device and having instructions for execution on the electronic device, the instructions comprising the steps of:
   providing at least one of the group of historical subject compliance data and historical protocol data;
   generating at least one predictive algorithm for predicting subject noncompliance by quantitative analysis of at least one of the group of the historical subject compliance data and the historical protocol data; and
   translating the at least one predictive algorithm into at least one prediction rule for use with a clinical trial.

26. The medium of claim 25 having instructions further comprising the steps of:
   obtaining subject compliance information; and
   comparing the subject compliance information to the at least one prediction rule to determine if action is needed.

27. The medium of claim 25, wherein the step of obtaining includes the use of a portable electronic device capable of displaying information and receiving and storing input from a user.

28. The medium of claim 25 having instructions further comprising the step of creating an evaluability database adapted to store data related to subject compliance.

29. A medium suitable for use in an electronic device and having instructions for execution on the electronic device, the instructions comprising the steps of:

providing at least one of the group of historical subject compliance data and historical protocol data;

generating at least one algorithm reflective of at least one of the group of the historical subject compliance data and the historical protocol data by quantitative analysis of the historical subject compliance data and the historical protocol data;

translating the at least one algorithm into at least one decision rule for analyzing subject compliance information;

obtaining the subject compliance information; and comparing the subject compliance information to the at least one decision rule to determine if corrective action is needed.

30. The medium of claim 29 having instructions further comprising the step of determining an appropriate corrective action if the step of comparing indicates that corrective action is needed.

31. The medium of claim 29, wherein the step of obtaining includes using a portable electronic device capable of displaying information and receiving and storing input from a user.

32. The medium of claim 29, wherein the step of generating employs at least one of the group of multiple linear regression, discriminant function analysis, logistic regression, neural networks, classification trees and regression trees.

33. A medium suitable for use in an electronic device and having instructions for execution on the electronic device, the instructions comprising the steps of:

providing historical subject compliance data and historical protocol data;

generating a spectrum of noncompliance representative of the historical subject compliance data not compliant with the historical protocol data by quantitative analysis of the historical subject compliance data and the historical protocol data;

obtaining subject compliance information; and comparing the spectrum of noncompliance to the subject compliance information to determine if corrective action is needed.

34. The medium of claim 33 having instructions further comprising the step of determining an appropriate corrective action if the step of comparing indicates that corrective action is needed.

35. The medium of claim 34, wherein the step of obtaining includes using a portable electronic device capable of displaying information and receiving and storing input from a user.

36. A medium suitable for use in an electronic device and having instructions for execution on the electronic device, the instructions comprising the steps of:

providing historical subject compliance data and historical protocol data;

generating at least one fraud detection algorithm for detecting subject fraud by quantitative analysis of the historical subject compliance data and the historical protocol data; and translating the at least one fraud detection algorithm into at least one fraud detection rule for use with a clinical trial.

37. A medium suitable for use in an electronic device and having instructions for execution on the electronic device, the instructions comprising the steps of:

providing subject compliance data;

generating at least one fraud detection algorithm for detecting subject fraud by quantitative analysis of the compliance data; and translating the at least one fraud detection algorithm into at least one fraud detection rule for use with a clinical trial.

* * * * *